United States Patent
Carlisle et al.

(10) Patent No.: US 11,914,401 B2
(45) Date of Patent: *Feb. 27, 2024

(54) AIRFLOW-BASED VOLUMETRIC PUMP

(71) Applicant: Pneuma Systems Corporation, Portsmouth, NH (US)

(72) Inventors: Jeffrey A. Carlisle, Portsmouth, NH (US); Timothy S. Schroeder, Rochester, NH (US); Thomas C. Plummer, Henniker, NH (US)

(73) Assignee: Pneuma Systems Corporation, Portsmouth, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/080,469

(22) Filed: Dec. 13, 2022

(65) Prior Publication Data

US 2023/0115695 A1 Apr. 13, 2023

Related U.S. Application Data

(63) Continuation of application No. 16/656,449, filed on Oct. 17, 2019, now Pat. No. 11,550,345.
(Continued)

(51) Int. Cl.
| | |
|---|---|
| *G05D 16/20* | (2006.01) |
| *G05B 19/042* | (2006.01) |
| *F04B 43/04* | (2006.01) |

(52) U.S. Cl.
CPC ......... *G05D 16/2013* (2013.01); *F04B 43/04* (2013.01); *G05B 19/042* (2013.01)

(58) Field of Classification Search
CPC .. G05D 16/2013; G05D 7/0688; F04B 43/04; F04B 13/00; F04B 2205/03;
(Continued)

(56) References Cited

U.S. PATENT DOCUMENTS

| 5,925,829 A | 7/1999 | Aragione et al. |
|---|---|---|
| 9,339,602 B2 | 5/2016 | Carlisle et al. |
(Continued)

FOREIGN PATENT DOCUMENTS

| CN | 208726441 U | 4/2019 |
|---|---|---|
| CN | 211327440 U | 8/2020 |
(Continued)

OTHER PUBLICATIONS

[No Author Listed] Elvie Pump | Silent, Wearable, Smart Breast Pump, retrieved from the internet under <https://www.elvie.com/en-us/shop/elvie-pump>, on Aug. 5, 2021, 12 pages.
(Continued)

*Primary Examiner* — Kidest Bahta
(74) *Attorney, Agent, or Firm* — Nutter McClennen & Fish LLP

(57) ABSTRACT

A system for precision liquid delivery includes a gas reservoir having a known volume. The system has a tightly load-coupled pneumatic driver (a "TLCP driver") that is configured to receive input power to cause the TLCP driver to move gas into the gas reservoir to produce a gas drive pressure. A valve is configured to couple the gas reservoir with a fluid reservoir having an unknown volume. The valve is further configured to selectively isolate or pneumatically couple pressures in the gas reservoir and the fluid reservoir. A gas-fluid interface couples pressure in the fluid reservoir to pressure in a fluid path. The fluid path is configured so that the fluid drive pressure driving the liquid in the fluid path is substantially the same as the fluid reservoir pressure. The system also has a pressure sensor configured to detect pressure in the gas reservoir and/or the fluid reservoir.

20 Claims, 8 Drawing Sheets

Related U.S. Application Data

(60) Provisional application No. 62/746,558, filed on Oct. 17, 2018.

(58) Field of Classification Search
CPC ...... F04B 43/073; G05B 19/042; A61M 5/14; F04F 1/06; G01F 1/34; G01F 13/006; G01F 22/02

See application file for complete search history.

(56) References Cited

U.S. PATENT DOCUMENTS

| | | |
|---|---|---|
| 10,173,003 B2 | 1/2019 | Davis |
| 10,342,920 B2 | 7/2019 | Carlisle et al. |
| 2003/0105536 A1* | 6/2003 | Corbelli ............... G05B 13/042 700/20 |
| 2003/0194328 A1 | 10/2003 | Bryant et al. |
| 2004/0073161 A1 | 4/2004 | Tachibana |
| 2004/0152944 A1 | 8/2004 | Medvedev et al. |
| 2008/0142093 A1* | 6/2008 | Turner .................. F15B 21/048 137/512 |
| 2009/0308484 A1 | 12/2009 | Nakagawa et al. |
| 2012/0265144 A1* | 10/2012 | Kalpin ............... A61M 5/14276 604/140 |
| 2013/0102974 A1 | 4/2013 | Davis et al. |
| 2013/0153040 A1 | 6/2013 | Goto et al. |
| 2014/0091574 A1 | 4/2014 | Favy |
| 2014/0180084 A1 | 6/2014 | Vilks |
| 2014/0350511 A1 | 11/2014 | Carlisle et al. |
| 2015/0094649 A1 | 4/2015 | Gittard |
| 2015/0322970 A1 | 11/2015 | Tanaka |
| 2016/0228637 A1 | 8/2016 | Carlisle et al. |
| 2017/0089746 A1* | 3/2017 | Rossi .................... A61M 1/024 |
| 2018/0361040 A1 | 12/2018 | O'Toole et al. |
| 2020/0125124 A1 | 4/2020 | Carlisle et al. |
| 2021/0402082 A1 | 12/2021 | Carlisle et al. |
| 2022/0118178 A1 | 4/2022 | Carlisle et al. |

FOREIGN PATENT DOCUMENTS

| | | |
|---|---|---|
| EP | 1150105 A2 | 10/2001 |
| EP | 3069641 A1 | 9/2016 |
| JP | 5629277 B2 | 11/2014 |
| WO | 2014190188 A2 | 11/2014 |
| WO | 2020081846 A1 | 4/2020 |

OTHER PUBLICATIONS

[No Author Listed] Murata Manufacturing Co., Ltd.—Microblower (Air Pump) <https://www.murata.com/en-us/products/mechatronics/fluid>, article accessed Oct. 30, 2019, 4 pages.

European Patent Office, Supplementary Search Report for Application No. 19872718.2, dated Jun. 14, 2022, 8 pages.

International Search Report and Written Opinion for International Application No. PCT/US2019/056783, dated Jan. 6, 2020, 13 pages.

International Search Report and Written Opinion for International Application No. PCT/US2021/055906, dated Jan. 26, 2022, 9 pages.

International Search Report and Written Opinion for International Application No. PCT/US2021/039649 dated Dec. 30, 2021, 23 pages.

\* cited by examiner

AIRFLOW-BASED VOLUMETRIC PUMP

PRIORITY

This patent application is a continuation of U.S. patent application Ser. No. 16/656,449, filed Oct. 17, 2019, which claims priority from provisional U.S. patent application No. 62/746,558, filed Oct. 17, 2018, entitled, "AIRFLOW-BASED VOLUMETRIC PUMP," and naming Jeffrey A. Carlisle, Timothy S. Schroeder, Thomas C. Plummer, Timothy O. Morales, and John C. Toomey as inventors, the disclosures each of which are incorporated herein, in their entirety, by reference.

FIELD OF THE INVENTION

Illustrative embodiments generally relate to a fluid pump and, more particularly, the illustrative embodiments relate to a tightly load-coupled pneumatic driver for the same.

BACKGROUND OF THE INVENTION

A variety of known pumps are used for fluid dispensing in laboratory and medical settings. In the laboratory, pumps and pipettes are commonly used for both aspiration and dispensing of samples, reagents, chemicals, solutions, and other liquids. In medical applications, pumps are useful for providing medicaments to patients, especially for the delivery of medical therapies requiring an extended period of time and through various routes of delivery, including intravenously, intra-arterially, subcutaneously, intradermally, intraperitoneally, in close proximity to nerves, and into an intraoperative site, epidural space or subarachnoid space. In addition to medication delivery, pumps are also commonly found in hospital pharmacies drug compounding applications, especially with highly complex parenteral nutrition compounded solutions. In laboratory applications, fluid pumps are general purpose tools often in the form of syringe pushers or tube based peristaltic pumps.

SUMMARY OF VARIOUS EMBODIMENTS

In accordance with one embodiment of the invention, a system for precision liquid delivery includes a gas reservoir having a known volume. The system also includes a tightly load-coupled pneumatic driver (a "TLCP driver") that is configured to receive input power that causes the TLCP driver to move gas into the gas reservoir to produce a gas drive pressure. The system also has a valve configured to couple the gas reservoir with a fluid reservoir having an unknown volume of a liquid. The valve is further configured to selectively isolate or pneumatically couple pressures in the gas reservoir and the fluid reservoir. The system furthermore has a gas-fluid interface that couples pressure in the fluid reservoir to pressure in a fluid path. The fluid path is configured so that the fluid drive pressure driving the liquid in the fluid path is substantially the same as the fluid reservoir pressure. The system also has a pressure sensor configured to detect pressure in the gas reservoir and/or the fluid reservoir.

The system may include a power controller configured to control the input power to the TLCP driver to adjust the gas drive pressure Furthermore, the gas drive pressure may cause the liquid in the fluid path to move at a selected flow rate when the pressures in the gas reservoir and the fluid reservoir are pneumatically coupled. The power controller may further be configured to control the input power to the TLCP driver to adjust the gas drive pressure to achieve the selected flow rate. To that end, the power controller may be operably coupled with the pressure sensor to receive the amount of pressure in one or both the gas reservoir and the fluid reservoir.

In some embodiments, the system includes a volume calculation engine that is configured to calculate the volume of liquid in the fluid reservoir. The volume calculation engine may also calculate fluid flow as a function of a corresponding change in pressure to pneumatically isolated fluid reservoir. In instances where the system maintains pressure constant, the volume calculation engine may use the changes in input power to the TLCP driver to calculate fluid flow as pressure remains substantially constant. In some embodiments, the gas drive pressure is adjusted as a function of the amount of pressure in one or both the gas reservoir and the fluid reservoir.

Among other things, the TLCP driver of the system may be formed from piezoelectric material. For example, the piezoelectric material may include ceramics. The TLCP driver may be a microblower in some embodiments. The gas-fluid interface may include a flexible membrane that imposes no stretching forces. The system may also include a second valve configured to selectively isolate or pneumatically couple the TLCP driver and the gas reservoir.

In accordance with another embodiment, a method determines fluid flow characteristics in a liquid delivery system. The method produces a gas drive pressure at a given value from a TLCP driver by providing an input power to move gas into a gas reservoir having a known volume. The gas drive pressure is configured to move fluid in a fluid reservoir. The pressure in the gas reservoir is measured to provide a gas reservoir pressure, and the pressure in the fluid reservoir is measured to provide a fluid reservoir pressure. The gas reservoir and a fluid reservoir are pneumatically coupled by opening a valve therebetween so that the gas reservoir pressure and the fluid reservoir pressure become substantially the same. The pressure in the gas reservoir and/or the fluid reservoir is measured after the gas reservoir and the fluid reservoir are pneumatically coupled. The method then calculates a pressure change in the gas reservoir, and a pressure change in the fluid reservoir. The method then calculates the volume of liquid within the fluid reservoir as a function of the pressure change in the fluid reservoir and the gas reservoir.

In some embodiments, the method pneumatically isolates the gas reservoir from the fluid reservoir by closing the valve therebetween. Flow rate out of a fluid path is determined by measuring pressure change in the fluid reservoir. Among other things, the method may detect an occlusion in the fluid path by measuring a change in the input power that is used to maintain the gas drive pressure at the given value. The system has a high sensitivity, and thus, may detect a change in work output of the TLCP driver of 0.1 to 1.0 percent. The method may control the input power to the TLCP driver to maintain constant work output.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, a tightly load-coupled pneumatic driver (a "TLCP driver"), such as one implemented as a microblower, produces a gas drive pressure that pumps fluid in accordance with a desired pressure and/or flow rate. The system enables rapid and precise changes in the gas drive pressure, and thus, in the pressure and/or flow rate of the pumped fluid. The TLCP driver generates differential pressure and flow of gas based on an electrical power input that is highly coupled to the work output (i.e., the mathematical product of pressure and flow). When the TLCP driver is used to maintain a constant pressure via a feedback control system, changes in flow rate compel a change in input power of comparable magnitude that is detectable by the system. Among other benefits, the TLCP driver provides highly sensitive fluid flow because it does not rely on mechanical linkages (e.g., gear box of a motor or leadscrews or tube-crushing fingers of peristaltic pump) for pumping the fluid.

Some conventional pumps (e.g., a syringe pump) require a backpressure of more than about 15 psi before an occlusion is detected. When the built-up pressure hits a predetermined threshold, the conventional pumps stop pumping. As another example, a peristaltic pump has an occlusion threshold of about 8 psi. Illustrative embodiments detect an occlusion from resultant pressure increases of less than about 1 psi.

In addition to providing high sensitivity, illustrative embodiments provide very precise pressure adjustments, as will be described further below. Conventional prior art pumps, such as a syringe pump, are not able to provide fine pressure adjustments (e.g., the syringe pump requires a significant application of force to overcome the stiction from the contact between the stopper and the inner wall of the syringe cylinder). Accordingly, conventional pumps may overcorrect when attempting to make fine pressure adjustments. In contrast, illustrative embodiments allow for fine pressure adjustments of about 0.1% to about 1.0% of drive pressure. Further advantages of illustrative embodiments include significant reduction in the size and weight of the pump relative to conventional syringe and peristaltic pumps. Details of illustrative embodiments are discussed below.

Figure 1:
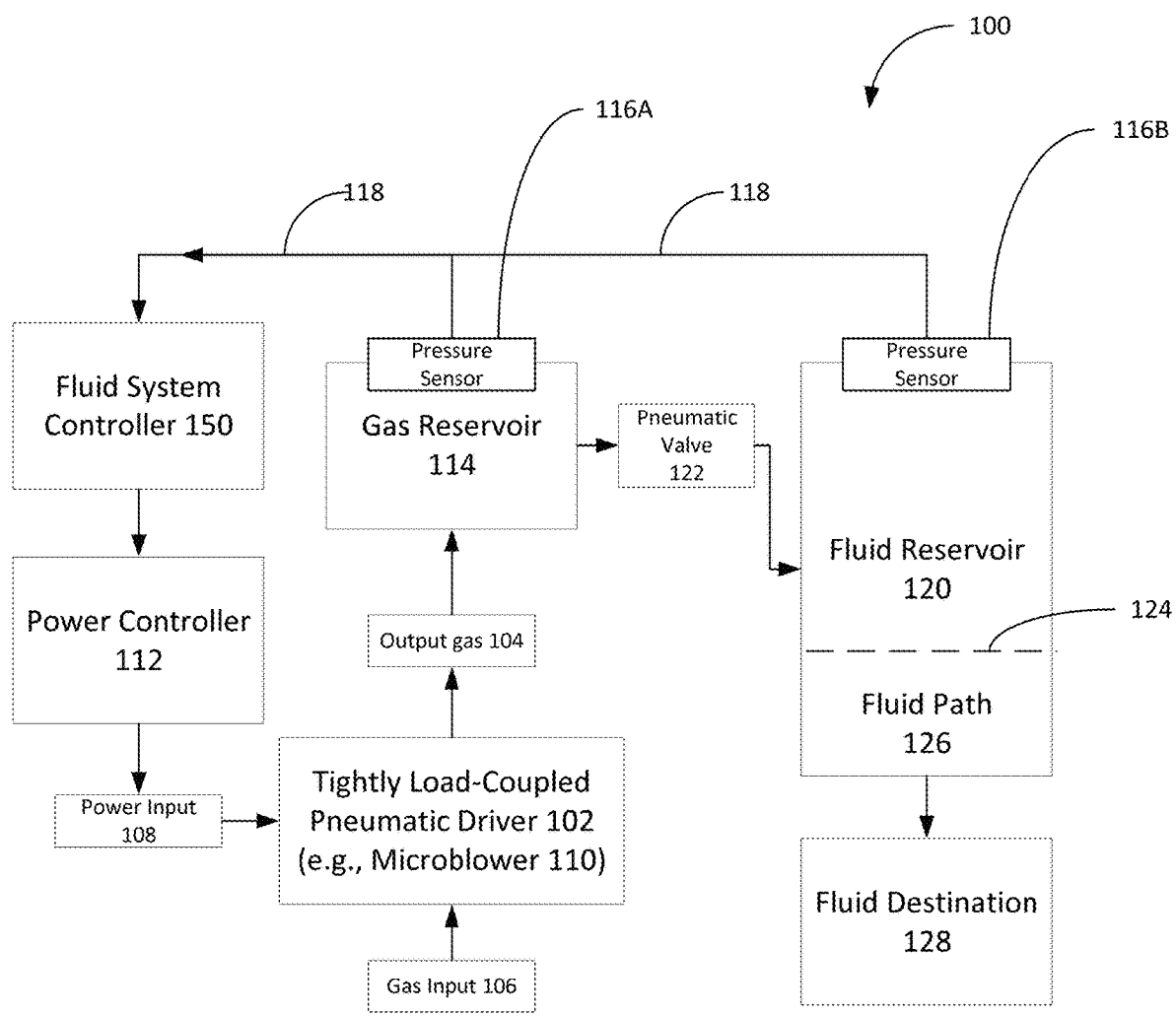
FIG. 1 schematically shows a system for fluid delivery in accordance with illustrative embodiments of the invention.

FIG. 1 schematically shows a system 100 for fluid delivery configured in accordance with illustrative embodiments of the invention. The system 100 has a TLCP driver 102, implemented as a microblower 110, that is configured to output gas 104 at a given drive pressure. The TLCP driver 102 is a pneumatic driver that is configured to generate differential pressure and flow of gas. Furthermore, the work output (i.e., the mathematical product of pressure and flow) is highly coupled to the electrical input power 108 provided to the TLCP driver 102. Thus, when the TLCP driver 102 is used in a feedback control system to maintain a constant pressure, changes in flow rate cause a change in input power 108 of comparable magnitude. In a similar manner, when the TLCP driver 102 is set to maintain a constant flow rate, changes in pressure cause a change in input power 108 of comparable magnitude.

While illustrative embodiments generally apply to any type of TLCP driver 102, some embodiments use a TLCP driver 102 known as a microblower 110. The microblower 110 functions as a TLCP driver 102 by using the vibration of piezoelectric material (e.g., ceramics) and preferably operates at its resonant frequency (most commonly in the ultrasonic range). The microblower 110 is a small device, generally weighing less than 10 grams and is suitable for pressures below 1 bar and flow rates below 1 L per minute. For discussion purposes, illustrative embodiments below refer to the microblower 110. However, it should be understood that any discussion of the microblower 110 may also apply more generally to the TLCP driver 102, and that reference to the microblower 110 is not intended to limit various embodiments. Accordingly, any discussion of the microblower 110 also refers to the TLCP driver 102, unless the context of the discussion otherwise requires.

To produce the gas drive pressure, the microblower 110 receives a gas input 106 (e.g., from filtered ambient air). The microblower 110 also receives the power input 108 from a power controller 112. As described previously, the work output of the TLCP driver 102 is highly coupled to the electrical input received. Thus, an increasing power input 108 produces a correspondingly larger work output by the microblower 110. This relationship may be approximately linear or have another relationship.

In illustrative embodiments, the gas output 104 of the microblower 110 is directed into a gas reservoir 114 having a known volume. Other embodiments can support the orientation of the TLCP driver 102 in the opposite direction to direct flow out from the gas reservoir 114 to the atmosphere. Further embodiments include a plurality of the TLCP drivers 102 and the valves to support bi-directional flow. The microblower 110 outputs the gas 104 at a given pressure and flow rate, as dictated by the input power 108. The gas reservoir 114 serves as the repository for the output gas 104 of the microblower 110. In some embodiments, the gas reservoir 114 may be a container having a known volume. However, in some other embodiments, the gas reservoir 114 may be and/or include the known volume of the tubing and/or other gas passageways downstream of the output of the microblower 110. In some embodiments, the gas reservoir 114 is coupled to a pressure sensor 116A that feeds a pressure signal 118 to the power controller 112.

The gas reservoir 114 is pneumatically coupled to a fluid reservoir 120. The fluid reservoir 120 may be, for example, within a bottle or vial, a syringe housing or a pipette tip. Accordingly, in illustrative embodiments, the volume of the fluid reservoir 120 may be the sum total of the volume of the interface 124, as well as the gas and the fluid separated by the interface 124. In illustrative embodiments, a pneumatic valve 122 selectively couples or isolates the gas reservoir 114 and the fluid reservoir 120. When the gas reservoir 114 and the fluid reservoir 120 are pneumatically coupled, their pressures become substantially the same. The drive pressure from the output gas 104 directly acts upon the fluid-gas interface 124 without any substantial interface components that might otherwise attenuate pressure.

In various embodiments, the pneumatic valve 122 may be a manually controlled valve, a passively activated checkvalve, an electromagnetic solenoid valve, a memory-metal activated valve, or other valve that serves to selectively isolate or connect pneumatic spaces.

In various embodiments, the fluid reservoir 120 is a rigid container of a fixed size and may be full of liquid or may be partially filled with liquid and gas. Regardless of the ratio of the contents in the fluid reservoir 120, when the valve 122 is open, a fluid-gas interface 124 is formed. The fluid-gas interface 124 may be formed by direct contact of the gas with the fluid. However, in some other embodiments, the interface 124 may be formed from a flexible membrane (e.g., formed from polyurethane or polyisoprene) that imposes no stretching forces. The membrane may be elastic but does not stretch. In that way, the system 100 allows the gas pressure to be substantially identical to the fluid.

In illustrative embodiments, the fluid path 126 is separated from the gas in the fluid reservoir 120 using a flexible membrane as the gas-fluid interface 124. For example, the flexible membrane gas-fluid interface 124 may be used in applications where the system 100 is subject to changes in orientation, such as inverting the system 100, so that the gas and the liquid would otherwise become interchanged. Other use examples for the flexible membrane gas-fluid interface 124 also include applications where the fluid path 126 cannot be exposed to gas in the fluid reservoir 120 because of concerns about sterility or contamination of the fluid.

As described previously, substantially all of the drive pressure from the gas reservoir 114 acts on the fluid in the fluid reservoir 120. This is in contrast to prior art methods known to the inventors that attenuate pressure (e.g., because of mechanical connections in a motor or from stretching of an elastic interface material). Thus, when the gas reservoir 114 and the fluid reservoir 120 are pneumatically coupled, the pressure generated by the microblower 110 is substantially the same as the pressure in the fluid reservoir 120, and the fluid in the fluid reservoir 120 therefore is driven at a known pressure. Accordingly, a pressure sensor 116B coupled to the fluid reservoir 120 may be used to monitor the pressure of the system 100 in addition to, or alternatively, to the pressure sensor 116A.

Furthermore, because the pump system 100 is pneumatically driven, it is more energy efficient and sensitive to small pressure adjustments than prior art pumps known to the inventors (e.g., using a stepper motor, or a syringe pump). For example, a stepper motor uses mechanical linkages that are not able to provide small adjustments in pressure. As another example, syringe pumps similarly are not able to produce small adjustments in pressure because of friction caused by the interface between the syringe walls and the stopper sliding therein. Furthermore, because both of these described prior art pumps have a large activation energy requirement, they cannot be considered to operate substantially instantaneously (e.g., at an ultrasonic frequency) as with the TLCP driver 102. In contrast, the output of the TLCP driver 102 is fluidly coupled to the input of the fluid path 126. Furthermore, the gas drive pressure does not have to overcome the forces of friction associated with traditional motors.

While the drive pressure created by the flow of gas may be substantially effectively frictionless (i.e., extremely low friction), resistance is encountered as the drive pressure moves the fluid in the fluid path 126 towards a fluid destination 128 (e.g., a patient receiving a medication). The resistance may be caused by, for example, viscous losses in the fluid path 126 line and/or an obstruction in the fluid path 126. In illustrative embodiments, increased resistance in the line causes an increase in pressure that is detected by the pressure sensor(s) 116A and/or 116B. The increase in pressure is instantaneously detected and fed back to the fluid system controller 150. The fluid system controller then controls the operation of the power controller 112 in a desired manner. Specifically, as noted above, in illustrative embodiments, the power controller 112 adjusts the electrical power input 108 as a function of the pressure signal(s) 118 so that the pressure may remain constant. In some other embodiments, the power controller 112 may adjust the electrical power input 108 so that flow rate in the fluid path 126 remains constant. In illustrative embodiments, the power controller 112 adjusts the input power on the same time scale as the pressure sensor, which is on the order of 200 samples per second. In some embodiments, the pressure sensor(s) may have a sampling rate of 0.1 to 200 samples per second. The power controller 112 may operate on the same or a similar timescale.

Figures 2A, 2B:
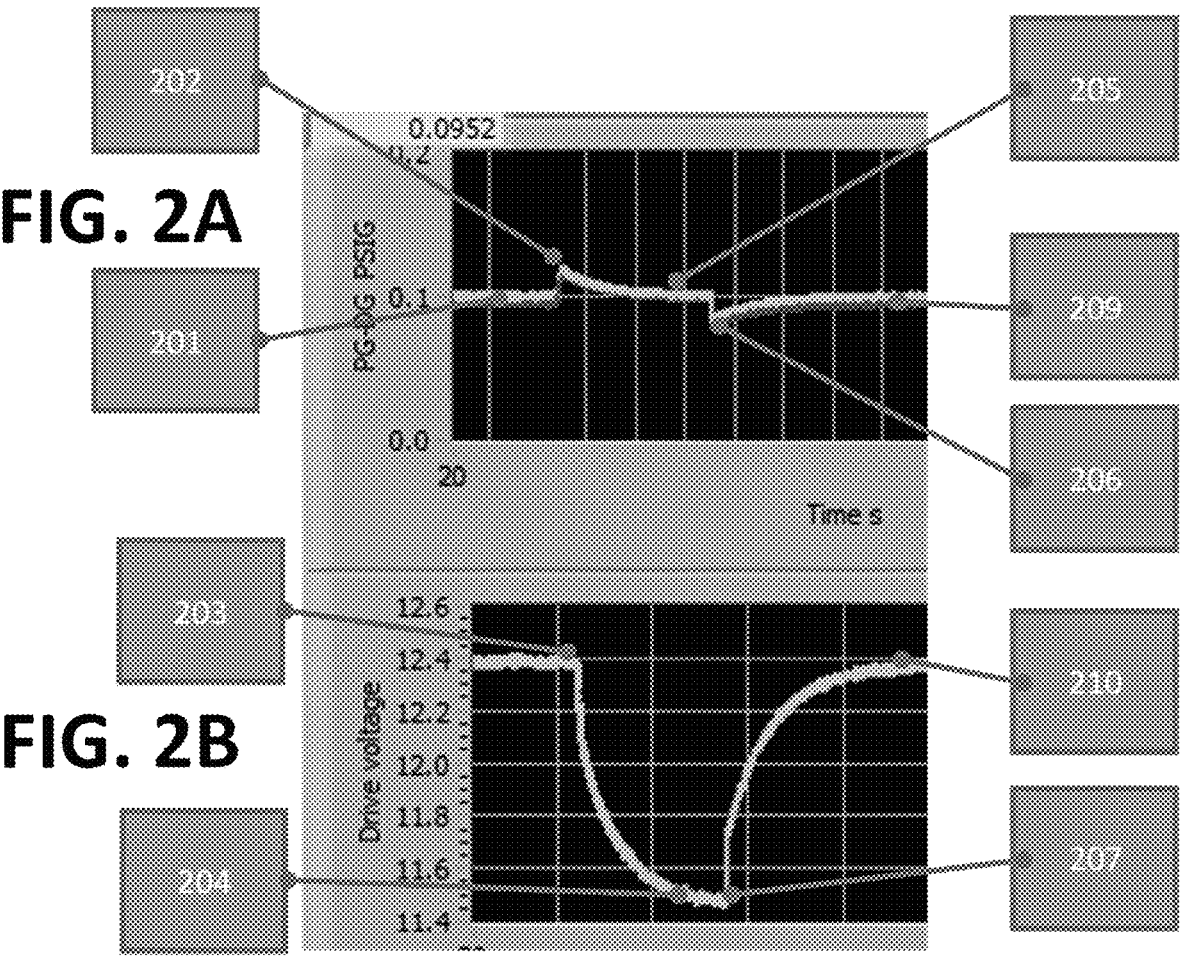
FIG. 2A schematically shows a chart of pressure over time in the system of FIG. 1.
FIG. 2B schematically shows a chart of drive voltage input for the system of FIG. 2A.

FIG. 2A schematically shows a chart of pressure over time in the system 100 of FIG. 1. FIG. 2B schematically shows a chart of drive voltage input for the system 100 of FIG. 2A over a period of seconds. At point 201, a constant work output is maintained by a constant drive pressure produced by the microblower 110. At point some, the fluid path 126 may become occluded or encounter increased resistance. The increased resistance results in a build-up in the path 126, and thus, an increased pressure (shown at point 202). It should be noted that in the example illustrated in the chart, the change is pressure is approximately 0.02 PSI, a change that is considered to be effectively invisible to conventional prior art pumping systems.

In illustrative embodiments, the power controller 112 is configured to keep pressure constant, and thus, the system 100 may compensate by approximately simultaneously decreasing the drive voltage input (starting at point 203). The power controller 112 adjusts the input power on the same time scale of the pressure sensor, which is on the order of 200 samples per second. The drive voltage decreases (e.g., at point 204), until it is sufficiently low (at point 204) for pressure to normalize at point 205. While the changes between input voltage 108 and pressure may not be 1:1, they generally are on the same order of magnitude and maintain proportionality.

In some embodiments, the power controller 112 may increase drive voltage, which increases drive pressure to maintain a constant work output of the microblower 110. When the occlusion/resistance is removed, the drive pressure has a rapid decrease (e.g., at point 206). The power controller 112 may be configured to increase the drive voltage (e.g., beginning at point 207) to cause pressure to return to the set value (e.g., at point 209), at which point the drive voltage remains steady (e.g., at point 210).

Most conventional prior art pump systems known to the inventors operate at a constant speed with a geared mechanical system. If the flow resistance increases, the back pressure increases. However, the power input to the system does not change significantly. In contrast, illustrative embodiments of the system 100 are configured to maintain a substantially constant pressure. Because of the sensitivity of the TLCP driver 102, changes to the power input required to maintain the pressure may be substantially instantaneously observed and adjusted.

In illustrative embodiments, the TLCP driver 102 detects occlusions or other resistance changes in the fluid path 126. In a conventional pump, the pump continues at its constant speed, and pressure against the occluded path builds up until it reaches a detectable alarm condition. When the occlusion releases, a large pressure induced bolus in undesirably released. It should be understood based on the previous discussion, that illustrative embodiments do not build up non-negligible pressures. Instead, the system 100 is configured to maintain pressure constant to virtually eliminate the potential risk and dangers of a pressure induced bolus. To that end, the TLCP driver 102 has substantially greater pressure sensitivity, allowing for substantially faster occlusion detection.

While the discussion of FIGS. 2A-2B refers to maintaining pressure constant within the system 100 as load changes, it should be understood that this is merely an example of how the system 100 may operate. In some other embodiments, the system 100 may be configured to maintain flow rate constant as load (e.g., resistance) increases. In a similar manner to the pressure example described previously, when resistance in the fluid path 126 increases, pressure in the fluid path 126 increases. The drive voltage may thus be increased (instead of decreased as in the previous example) to further increase flow rate.

Figure 3:
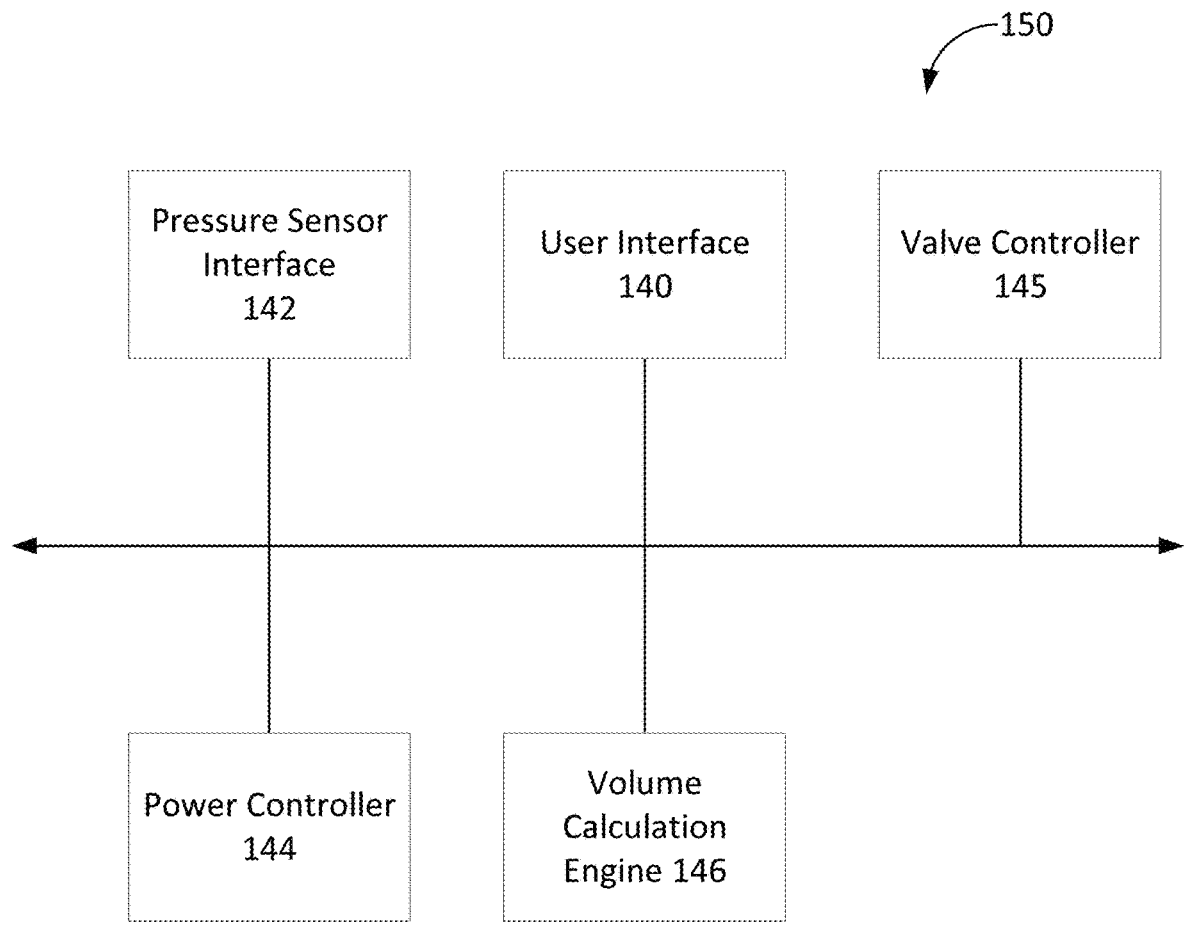
FIG. 3 schematically shows details of a fluid system controller in accordance with illustrative embodiments of the invention.

FIG. 3 schematically shows details of the fluid system controller 150 of FIG. 1 configured in accordance with illustrative embodiments of the invention. Each of these components is operatively connected by any conventional interconnect mechanism. FIG. 3 simply shows a bus communicating each the components. Those skilled in the art should understand that this generalized representation can be modified to include other conventional direct or indirect connections. Accordingly, discussion of a bus is not intended to limit various embodiments.

Indeed, it should be noted that FIG. 3 only schematically shows each of these components. Those skilled in the art should understand that each of these components can be implemented in a variety of conventional manners, such as by using hardware, software, or a combination of hardware and software, across one or more other functional components. For example, the power controller 144 (discussed in detail below) may be implemented using a plurality of microprocessors executing firmware. As another example, the power controller 144 may be implemented using one or more application specific integrated circuits (i.e., "ASICs") and related software, or a combination of ASICs, discrete electronic components (e.g., integrated circuits), and microprocessors. Accordingly, the representation of the power controller 144 and other components in a single box of FIG. 3 is for simplicity purposes only. In fact, in some embodiments, the power controller of FIG. 3 is distributed across a plurality of different components—not necessarily within the same housing or chassis.

It should be reiterated that the representation of FIG. 3 is a significantly simplified representation of an actual fluid system controller 150. Those skilled in the art should understand that such a device has other physical and/or functional components, such as central processing units, other packet processing modules, and short-term memory. Accordingly, this discussion is not intended to suggest that FIG. 3 represents all of the elements of the fluid system controller 150. In fact, much of what was said here with regard to FIG. 3 can also be applied to components of the system 100 of FIG. 1.

As described previously, the power controller 112 controls the power input 108 provided to the microblower 110. The fluid system controller 150 thus instructs the power controller 112 to provide the power input 108 to the microblower 110. Accordingly, the power controller 112 controls the pressure of the output gas 104. To that end, the fluid system controller 150 has a user interface 140 configured to receive an input from a user. For example, the user interface 140 may receive a setting of a constant pressure or a constant flow rate that the microblower 110 should output. In various embodiments, the user interface 140 may be provided as a touchscreen display, a mechanical interface, and/or as a smartphone connected application.

The fluid system controller 150 also has a pressure sensor interface 142 configured to receive pressure signals 118 from the noted pressure sensors 116A and 116B (or other pressure sensors). As described further below with reference to FIGS. 4A-4B, the pressure signals 118 provide a feedback loop to the fluid system controller 150 that allows the power controller 112 to adjust the power input 108 provided to the microblower 110 as a function of the amount of pressure in one or both the gas reservoir 114 and the fluid reservoir 120. Those skilled in the art will recognize that the feedback control loop can be substantially modified by, for example, adjusting coefficients for errors that are proportional, integrative, and derivative (PID). Such PID coefficients can even be modified during operation of the system 100, providing a wide dynamic range of behaviors.

The fluid system controller 150 also has a TLCP power input engine 144 configured to receive the settings from the user interface 140 (e.g., a constant pressure setting), receive pressure data from the pressure sensor interface 142, and to instruct the power controller 112 to increase or decrease pressure and/or flow rate. The power input engine 144 performs calculations relating to what power input 108 should be provided to the microblower in accordance with the desired pressure setting in the gas reservoir and/or the fluid reservoir 144. The power input engine 144 then provides that information to the power controller 112, that provides the power input 108 to the microblower. The fluid system controller 150 has a volume calculation engine 146 configured to calculate the unknown fluid volume in the fluid reservoir 120, based on the known volume in the gas reservoir, and the known pressures in the fluid reservoir 120 and the gas reservoir 114. In some embodiments, the fluid volume calculation engine 146 may also be configured to calculate the flow rate of fluid out of the fluid reservoir 120. Additionally, or alternatively, the volume calculation engine 146 may also be configured to measure fluid going into the fluid reservoir 120. Fluid flow directional references of gas or fluids should be considered to represent flow in either direction. The fluid system controller 150 also has a valve controller 145 that controls the opening and closing of the valve 122.

Figure 4A:
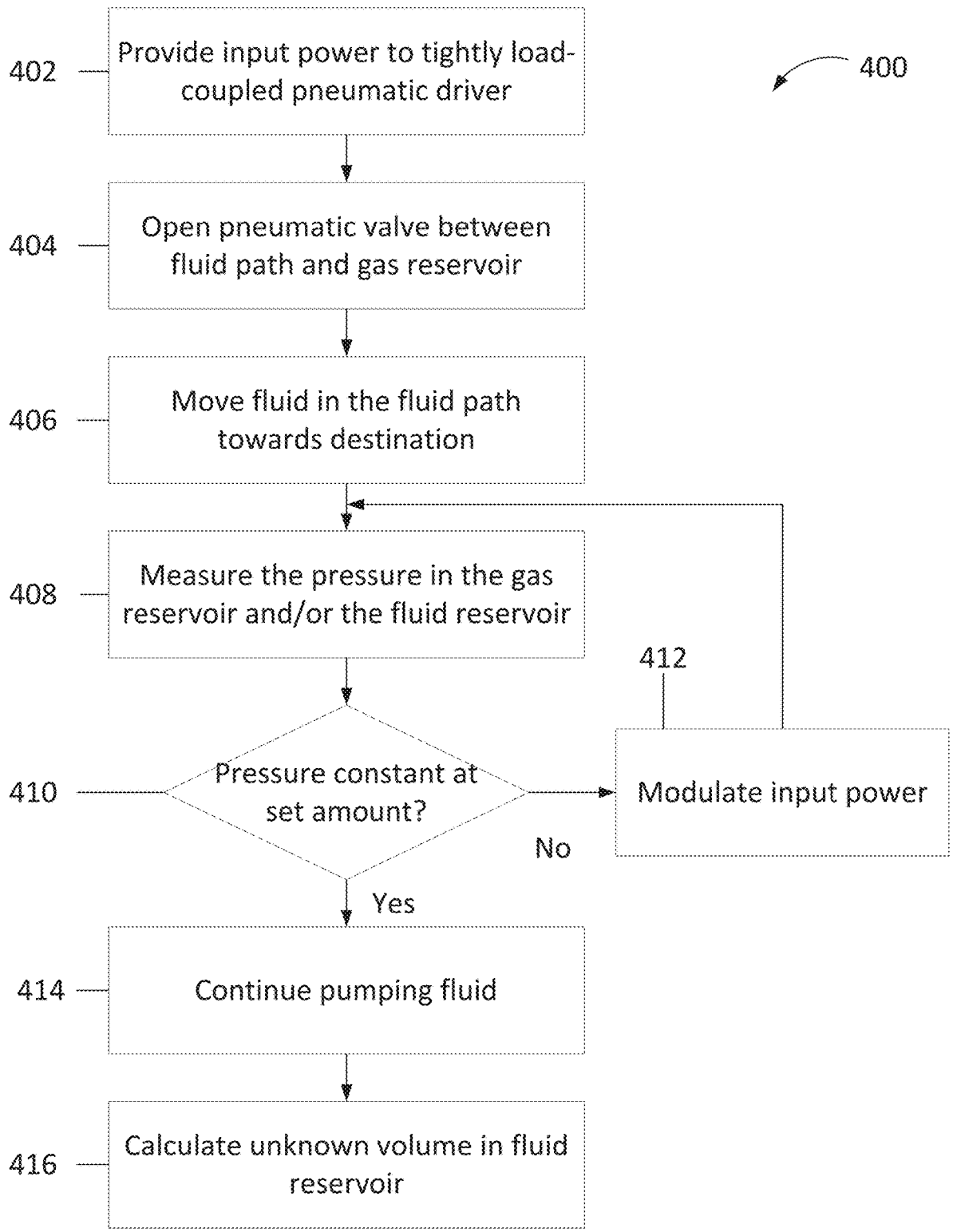
FIG. 4A shows a process of modulating the drive pressure inside a fluid system in accordance with illustrative embodiments of the invention.

FIG. 4A shows a process of modulating the drive pressure inside a fluid system 100 in accordance with illustrative embodiments of the invention. It should be noted that this method is substantially simplified from a longer process that may normally be used. Accordingly, the method shown in FIG. 4A may have many other steps that those skilled in the art likely would use. In addition, some of the steps may be performed in a different order than that shown, or at the same time. Furthermore, some of these steps may be optional in some embodiments. Accordingly, the process 400 is merely exemplary of one process in accordance with illustrative embodiments of the invention. Those skilled in the art therefore can modify the process as appropriate.

The process begins at step 402, which provides input power 108 to the TLCP driver 102. As described previously, the power input 108 is provided to the TLCP driver 102, and the TLCP driver 102 begins to pump gas in accordance therewith. Of course, as noted above, the pressure and flow of gas is a function of the input power 108. Thus, the input power 108 may be initially set, for example, by a user through the user interface 140. The microblower 110 then begins to pump the output gas 104 into the gas reservoir 114.

At step 404, the valve controller 145 optionally opens the pneumatic valve 122 between the fluid reservoir 120 and the gas reservoir 114. The fluid path 126 and the gas reservoir 114 thus become pneumatically coupled, and their pressures become substantially the same (e.g., because of the interface 124, which does not substantially attenuate the pressure). The gas drive pressure presses against the fluid at the interface 124, either directly, or via the flexible, inelastic membrane.

At step 406, the pressure in the fluid path 126 moves the fluid towards its destination 128. For example, the destination 128 may be a patient in a hospital setting who is receiving an IV infusion of a particular drug. In many instances, it is desirable to pump a fluid into the patient at, or less than, a specific flow rate and/or specific pressure. In prior art systems known to the inventors, fluid line occlusion undesirably goes largely undetected, resulting in large bolus administrations of drug after the occlusion is removed. Illustrative embodiments mitigate this problem by providing a self-regulating system that controls pressure and ensures that the patient receives the prescribed drug dosage in a safe manner.

To that end, the process moves to step 408, in which the pressure sensor 116B measures the pressure in the gas reservoir and/or the fluid path to determine whether pressure is constant at the set amount. As described previously, the system 100 is highly sensitive to even small changes in pressure (e.g., because of the lack of friction and/or mechanical gear components in the TLCP driver 102). The pressure readings (e.g., from pressure sensor 116A and/or 116B) are fed back to the fluid system controller 150 via the pressure sensor interface 142. The process then moves to step 410, which determines whether the pressure is constant at the specified level.

The fluid system controller 150 determines whether there is an occlusion or resistance in the line by looking at the pressure. As described with reference to FIGS. 2A-2B, the fluid system controller 150 may determine whether there is occlusion/resistance in the line by noticing a change in the pressure in the system (e.g., gas reservoir, fluid reservoir, and/or fluid line). However, in some embodiments, pressure is kept constant by the system 100. Accordingly, when the line is occluded, to maintain pressure constant, input power goes down. The change in input power 108 allows the system 100 to determine changes in flow/resistance while maintaining pressure constant. Thus, the system 100 may detect an occlusion while keeping pressure constant.

If the pressure measurement shows that the pressure is not at the specified amount, the process proceeds to step 412, in which the power controller 144 modulates the input power 108 toward an appropriate level. As such, the fluid system controller 150 determines that the pressure is not with at the correct setting and its power controller 144 sends a signal to the power controller 112 to make a corresponding adjustment to the output power 108. The process 400 then returns to step 400, which again measures the pressure. If the pressure is still incorrect, the process repeats. This may occur many times, and steps 408-412 may occur substantially simultaneously (e.g., pressure readings may be taken continuously). If the pressure reading is at the appropriate setting in step 410, then the system 100 continues to step 414 and pumps the fluid to the patient at the set pressure.

The operation of valve 122 may vary, but some embodiments open the valve 122 for a period on the order of 1 second to allow substantial equilibration between the pressure in the gas reservoir 114 and the pressure in the fluid reservoir 120. In some applications, the valve controller 145 may open the valve 122 for a small fraction of a second, allowing partial equilibrium of pressures.

In some embodiments, the process may optionally move to step 416, in which the volume calculation engine 146 calculates the unknown volume of fluid in the fluid reservoir 120. Although shown here at the end of the process, step 416 may additionally, or alternatively, be performed earlier in the process and multiple times throughout the process (e.g., in the feedback loop of steps 408-412). The volume calculation engine 146 may calculate the unknown volume by using, for example, the methodologies described below with reference to FIG. 5.

Figure 4B:
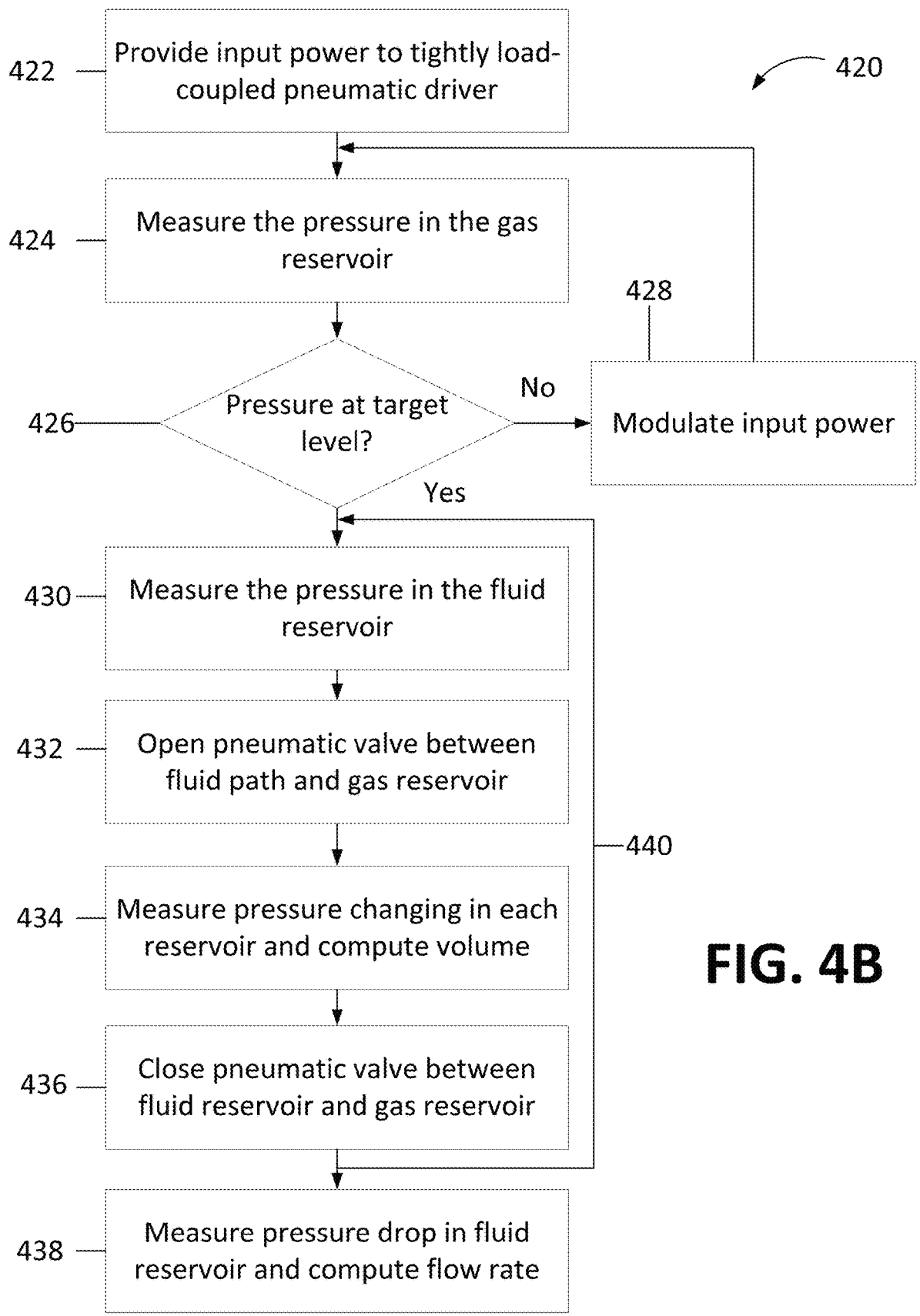
FIG. 4B shows a process of calculating the unknown volume of fluid in the fluid reservoir and measuring flow rate from the fluid reservoir in accordance with illustrative embodiments of the invention.

FIG. 4B shows a process 420 of calculating the unknown volume of fluid in the fluid reservoir 120 and measuring flow rate from the fluid reservoir 120 in accordance with illustrative embodiments of the invention. It should be noted that this method is substantially simplified from a longer process that may normally be used. Accordingly, the method shown in FIG. 4B may have many other steps that those skilled in the art likely would use. In addition, some of the steps may be performed in a different order than that shown, or at the same time. Furthermore, some of these steps may be optional in some embodiments. Accordingly, the process 420 is merely exemplary of one process in accordance with illustrative embodiments of the invention. Those skilled in the art therefore can modify the process as appropriate.

In a manner similar to the process 400 of FIG. 4A, the process 420 begins at step 422 by providing the power input 108 to the TLCP driver 102. As described previously, this target pressure may be set by the user using the user interface 140. At step 424 the process measures the pressure in the gas reservoir 114 using the pressure sensor 116A. The pressure sensor 116A passes the pressure data to the pressure sensor interface 142, and the fluid system controller 150 uses this data at step 426 to determine whether the pressure is at the target level.

If the pressure is not at the target level at step 426, then the process proceeds to step 428, where the input power 108 is modulated. This adjustment either increases or decreases the gas pressure output by the TLCP driver 102. This process may be repeated until the pressure in the gas reservoir 114 is at the target level. After the pressure in the gas reservoir 114 reaches the target level, the process proceeds to step 430, where the pressure in the fluid reservoir 120 is measured by the pressure sensor 116B. At this point in the process, the gas reservoir 114 and the fluid reservoir 120 are pneumatically isolated. The pressure data is fed to the fluid system controller 150 through the pressure sensor interface 142.

The process then proceeds to step 432, where the valve controller 145 opens the pneumatic valve 122 between the fluid reservoir 120 and the gas reservoir 114 to pneumatically couples the reservoirs. In some embodiments, the valve controller 145 may receive an indication of when to open and close the valve 122 from the volume calculation engine 146. As is shown later with reference to FIG. 6A-6C, pneumatically coupling the reservoirs 114 and 120 causes them to have substantially the same internal pressure. The process then measures the pressure (or the pressure changes) in each of the reservoirs 114 and 120, and the volume calculation engine 146 uses this data to compute the unknown gas volume in the fluid reservoir 120 based on the change in pressure. The volume calculation engine 146 may then subtract the calculated gas volume from the total known volume of the fluid reservoir 120 (e.g., 60 mL syringe housing) to calculate the previously unknown volume of fluid within the fluid reservoir 120.

The process then optionally proceeds to step 436, where the valve controller 145 closes the pneumatic valve 122 between the fluid reservoir 120 and the gas reservoir 114. At this point, the reservoirs 114 and 120 are no longer pneumatically coupled, and thus, pressure changes within one reservoir does not affect the pressure in the other reservoir. As fluid flows out of the fluid reservoir 120 through the fluid path 126, the pressure sensor 116B detects a pressure drop. At step 438, the volume calculation engine 146 may use this change in pressure along with the previously calculated volume from step 434 to determine the flow rate of the fluid from the fluid reservoir 120 (i.e., by watching the pressure "leak").

Additionally, or alternatively, to step 438, the process 420 may measure fluid flow by periodically calculating (e.g., every minute) the volume of liquid in the liquid reservoir 120 using the feedback loop 440. In a manner similar to the process described previously, the valve 122 may be reopened to combine the pressures of the two reservoirs 114 and 120, the volume calculation engine 146 may use the pressure change to calculate the volume of liquid in the liquid reservoir 120, and the change in volume may be used to determine flow rate at discrete sampling intervals. This process may be repeated for a plurality of cycles (e.g., by reopening the valve 122, taking a pressure measurement to calculate volume loss, and reclosing the valve 122).

Figure 5:
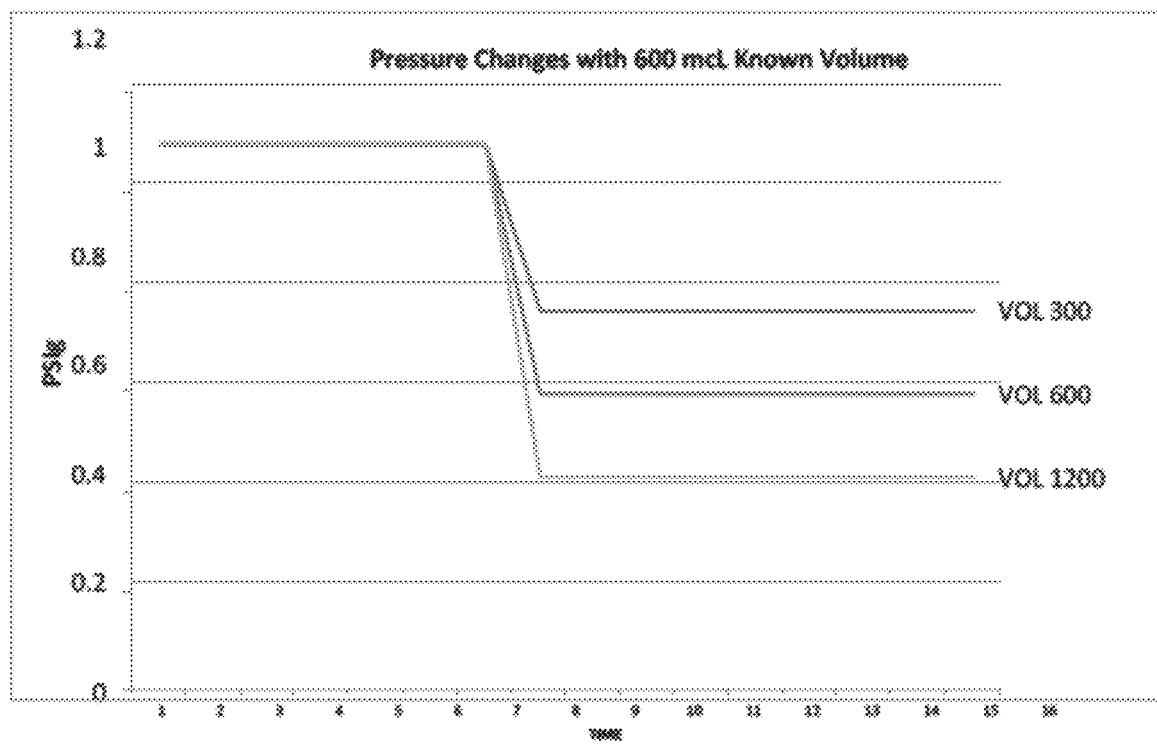
FIG. 5 provides an example of the volume calculations made by the volume calculation engine in accordance with illustrative embodiments of the invention

FIG. 5 provides an example of the volume calculations made by the volume calculation engine 146 in accordance with illustrative embodiments of the invention. The following examples are provided as an exemplary embodiment of the gas volume-based calculations that can be made by the system 100. The system 100 has a known volume (e.g., the gas reservoir 114) or a known volume change and an unknown volume. Illustrative embodiments also measure the pressures of the known volume(s) (or known volume changes) and the unknown volume(s), individually and after they are pneumatically combined according to the forgoing methods and modes of operation of the system 100.

Three examples are provided in the table of FIG. 5 with a known volume (e.g., the gas reservoir 114) of 600 microliters (mcL), and three respective (and different), unknown volumes—600 mcL, 300 mcL, and 1200 mcL. The figure shows the pressure signals 118 taken from the first pressure sensor 116A for the gas reservoir 114 and the second pressure sensor 116B for the resulting combined known (gas reservoir 114) and unknown (fluid reservoir 120) volumes, sitting respectfully at knowable and measurable pressures, and occurring at roughly time "7" on the x-axis timeline of the figure.

In the first example, labeled "600" (mcL) in the table and "VOL 600" in the figure shows an initial gauge pressure of 1 PSIg for the known volume (reference volume 114). The unknown volume(s) have a gauge pressure of 0 PSIg (as measured by second pressure sensor 116B). The value of the actual pressures of the two respective volumes is unimportant, as long as they are measurable and different. When the two volumes, known 114 and unknown 120 and 126, are combined at t=7, by opening the pneumatic valve 122, the pressure of the combined volumes is measured by one or both pressure sensors 116A and 116B, and are the same at that point in time, t. In this example (with the 600 mcL unknown volume), the resulting final combined pressure falls to exactly the midpoint (0.500 PSIg), between the two initial pressures of 1 PSIg (for the gas reservoir 114) and 0 PSIg (for the unknown volumes).

The known volume experienced a pressure change down from 1 PSIg to 0.5 PSIg=0.5 PSIg, and the unknown volume experienced a pressure change up from 0 PSIg to 0.5 PSIg=0.5 PSIg. The resulting ratiometric difference between the two is calculated by dividing the net pressure difference each respective volume experienced, 0.5/0.5=1. Accordingly, the unknown volume(s) can be calculated by multiplying the known volume (reference volume 114=600 mcL) by this ratio, 1, resulting in a calculated unknown volume of 600 mcL (i.e. 600 mcL*1=600 mcL). When two identical volumes with different known pressures are combined, the resulting combined pressure is expected to be the average of the two.

The second example, labeled "300" (mcL) in the table and "VOL 300" in FIG. 5 also shows an initial gauge pressure of 1 PSIg for the known volume (reference volume 114). Like in the previous example, the unknown volume has a measured (by the second pressure sensor 116B) gauge pressure of 0 PSIg. When combined according to the same mechanism as described in the previous example, the resulting final pressure of the combined volumes, as measure by one or both of the pressure sensors 116A and 116B, is measured to be 0.667 PSIg. Therefore, the known volume experienced a pressure change down from 1 PSIg to 0.667 PSIg=0.333 PSIg, and the unknown volume experienced a pressure change up from 0 PSIg to 0.333 PSIg=0.667 PSIg. The resulting ratiometric difference between the two is calculated by dividing the net pressure difference each respective volume experience, 0.333/0.667=0.5. Accordingly, the unknown volume(s) can be calculated by multiplying the known volume (gas reservoir 114=600 mcL) by this ratio, 0.5, resulting in a calculated unknown volume of 300 mcL (i.e., 600 mcL*0.5=300 mcL). This is because a larger volume at a high pressure is combined with a smaller volume at a lower pressure, and the resultant combined pressure is closer to the higher pressure of the larger volume. Referring still to FIG. 5, the third example, labeled "1200" (mcL) in the table and "VOL 1200" in the figure also shows an initial gauge pressure of 1 PSIg for the known volume (reference volume 114). Like in the previous two examples, the unknown volume has a measured (by second sensor 116B) gauge pressure of 0 PSIg. And, when combined according to the same mechanism as described in two previous examples, the resulting final pressure of the combined volumes, as measure by one or both of the pressure sensors 116A and 116B, is measured to be 0.333 PSIg. Therefore, the known volume experienced a pressure change down from 1 PSIg to 0.333 PSIg=0.667 PSIg, and the unknown volume experienced a pressure change up from 0 PSIg to 0.667 PSIg=0.333 PSIg. The resulting ratiometric difference between the two is calculated by dividing the net pressure difference each respective volume experience, 0.667/0.333=2.0. Accordingly, the unknown volume(s) can be calculated by multiplying the known volume (reference volume 114=600 mcL) by this ratio, 2.0, resulting in a calculated unknown volume of 1200 mcL (i.e., 600 mcL*2=1200 mcL). This makes intuitive sense, since when a larger volume at a low pressure is combined with a smaller volume at a higher pressure, one would expect the resultant combined pressure to be closer to the lower pressure of the larger volume.

As a verification for the use of this ratiometric calculation and methodology, reference is made to the Ideal Gas Law (PV=nRT), where the mathematical product of the absolute pressure (P) multiplied by the volume (V) should remain constant if the amount of gas is unchanged. Here, it is assumed in the instant example the absolute temperature (T) remains constant. With two volumes, one can take the sum of the PV values and compare it to the PV of the final combined volumes. In this formula, the pressures must be absolute pressures, yet for the ratiometric calculation gauge pressure measurements are sufficient since one is only comparing the ratios of pressure changes. Therefore, to verify the ratiometric calculation and methodology, referring to the first example, and the corresponding first column of the table in FIG. 5, the measured atmospheric pressure is 14.700 PSIa; the known volume is 600 mcL (although the unit of measure is not relevant in this verification); the unknown volume is 600 mcL. Initially, the pressure in the known volume is measured as 1 PSIg. Therefore, the PV calculation for the combined volumes is ((14.700+1)*600+ (14.700+0)*600)=18,240. Knowing that the combined volume is 1,200, the expected pressure ("Final Pressure PSIa") in the combined volume is 18,240/1,200=15.2 PSIa. Subtracting the atmospheric pressure of 14.7 PSIa, one is left with a gauge pressure of 0.5 PSIg. Accordingly, a similar verification in kind is found for the second and third examples in the second and third columns of the table in FIG. 5, for unknown volumes of 300 mcL and 1200 mcL, respectively.

Due to the modularity of the system 100 and in particular of the pneumatic drive components (e.g., microblower(s) 110, pneumatic valve 122, first pressure sensor 116A, and second pressure sensor 116B), illustrative embodiments may be applied to a broad and complex set of use cases by adding additional pneumatic drive components. For example, to deliver liquid to multiple channels in a parenteral nutrition pharmacy compounder, a discrete set of pneumatic drive components may be added to each channel.

Figure 6A:
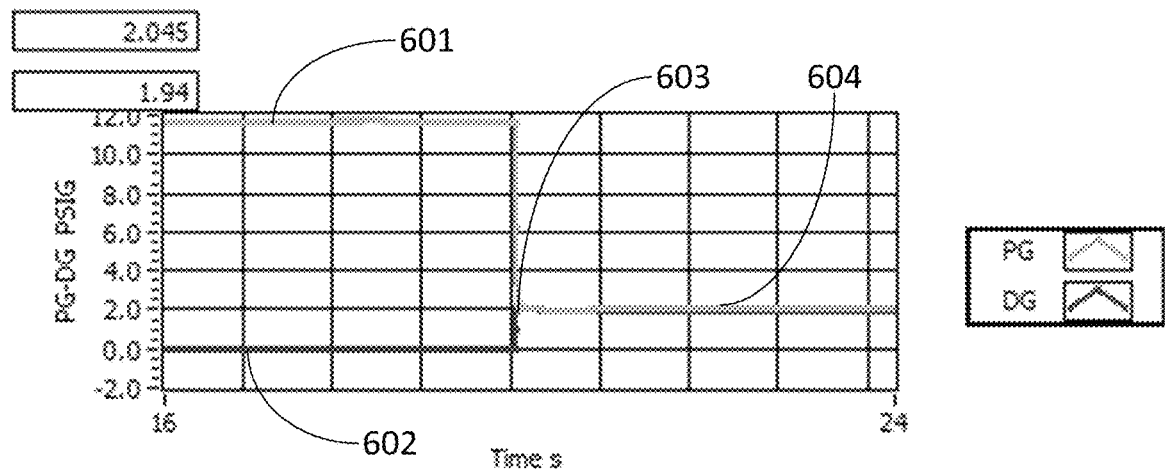
FIGS. 6A-6C show an example of the pressure measurements in the gas reservoir and the fluid reservoir before and after they are pneumatically coupled in accordance with illustrative embodiments of the invention.
Figure 6B:
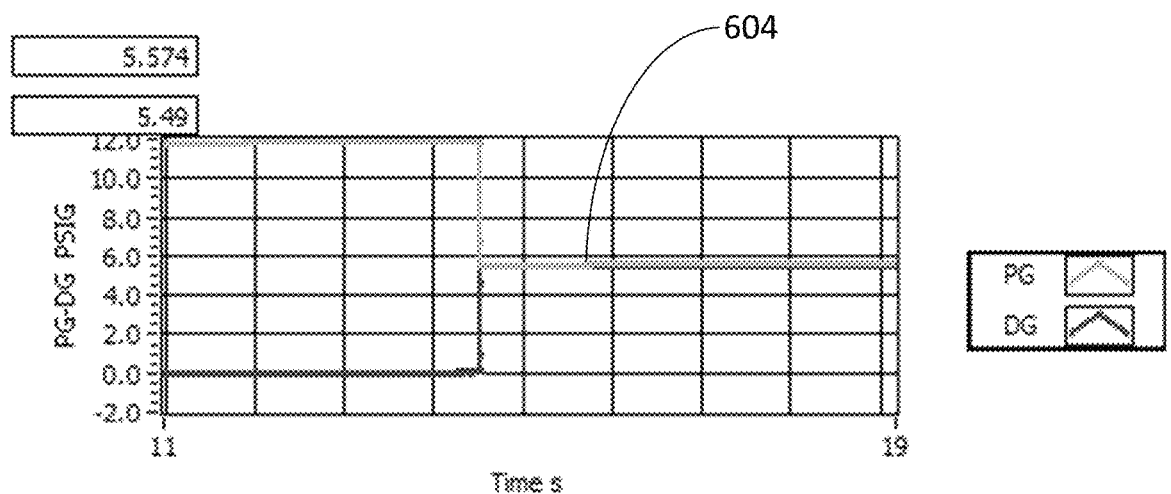
Figure 6C:
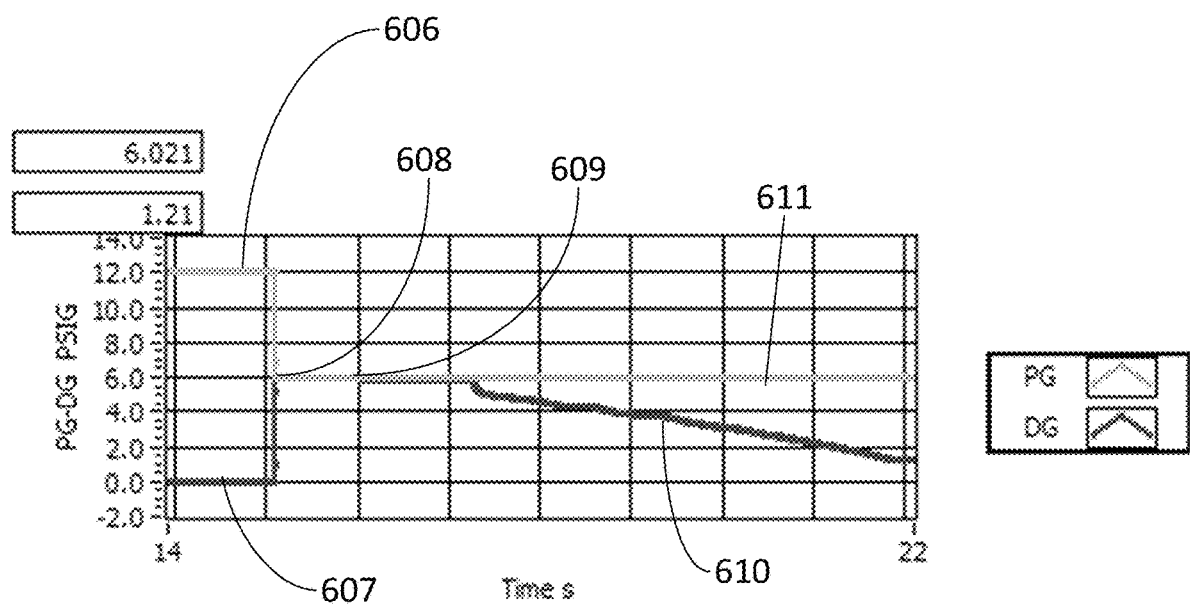

FIGS. 6A-6C show examples of pressure measurements in the gas reservoir 114 and the fluid reservoir 120 before and after they are pneumatically coupled in accordance with illustrative embodiments of the invention. In these figures, the gas reservoir 114 has a know volume and a measured pressure 601. The fluid reservoir 120 has an unknown volume and a measure pressure 602. In FIGS. 6A and 6C, pressures 602 and 607 are at 0 PSIg merely because they had been opened to atmosphere prior to the process. In illustrative embodiments, the analysis of pressure changes do not require any restriction on the initial conditions, except that the pressures in the gas and fluid reservoirs 114 and 120 are different than each other prior to the opening of valve 122. At point 603, the valve 122 is activated to pneumatically join the two reservoirs 114 and 120, and the two pressures combine to have a measured pressure 604. The relationship between the measured pressures of both reservoirs 114 and 120 and the known volume of one reservoir 114 can be used to calculate the volume of the other reservoir 120.

FIG. 6B shows a different example of the fluid reservoir 120 being joined with the gas reservoir 114. Again, the volume of the gas reservoir 114 may be known. Joining the two reservoirs 114 and 120 results in a joined pressure 605. As can be seen from FIGS. 6A-6B, the reservoir with the larger volume has a greater overall effect on joined pressure. For example, in FIG. 6A the larger volume is the fluid reservoir 120, whereas in FIG. 6B, the two volumes are about the same.

In FIG. 6C, the gas reservoir 114 has a known volume and a measured pressure 606. The fluid reservoir 120 has an unknown liquid volume and a measured pressure 607. At a point of time 608, the valve 122 is activated to pneumatically join the two reservoirs 114 and 120. The resultant pressure 609 can be measured, and the unknown liquid volume can be calculated by the volume calculation engine 146. After point 608, the pneumatic valve 122 may be closed by the valve controller 145. Thus, each reservoir remains pressurized at substantially the same pressure as when the reservoirs 114 and 120 were coupled. However, as fluid flows from the fluid reservoir 120, the pressure in the fluid reservoir 120 decreases. This change in pressure is shown in line 610, whereas the pressure in the gas reservoir 114 remains constant (shown by line 611). The change in absolute pressure represents the proportional change in volume over time, or flow. Accordingly, in illustrative embodiments the volume calculation engine 146 may be used to calculate flow out of the system 100 over the time (i.e., fluid flow rate).

A person of skill in the art understands that illustrative embodiments provide a number of advantages. For example, illustrative embodiments include a much more rapid and precise response to pressure changes over prior art pumps known to the inventors. This is, for example, because some conventional pumps have a small motor and a gear box. Illustrative embodiments provide a high-frequency, self-resonating driver where a change in the load is seen directly by the system 100. Because there is no substantial interference with the coupling between the drive pressure and the liquid in the fluid reservoir (including the interface 124 which is flexible and negligible) when the valve 122 is open, the gas pressure is substantially the same as the liquid pressure. This intimate connection allows the system 100 to be delicately balanced. A further advantage of the system 100 is that line occlusion and/or changes in resistance may be detected while keeping pressure constant (e.g., by detecting a change in input power 108).

It should be understood that the term fluid encompasses liquids. The term "liquid" may be applied throughout the previous description to replace the term "fluid," for example, to refer to the fluid reservoir 120 and the gas-fluid interface 124.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, programmable analog circuitry, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

Disclosed embodiments, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A system for precision liquid delivery, the system comprising:
    a gas reservoir having a known volume;
    a tightly load-coupled pneumatic driver (a "TLCP driver") configured to receive input power causing the TLCP driver to move gas into the gas reservoir to produce a gas drive pressure;
    a valve configured to couple the gas reservoir with a fluid reservoir having an unknown volume of a liquid, the valve further configured to selectively isolate or pneumatically couple pressures in the gas reservoir and the fluid reservoir;
    a gas-fluid interface that couples pressure in the fluid reservoir to pressure in a fluid path, the gas-fluid interface configured so that the fluid drive pressure driving liquid in the fluid path is substantially the same as the fluid reservoir pressure; and
    a pressure sensor configured to detect pressure in the gas reservoir and/or the fluid reservoir.

2. The system of claim 1, further comprising a power controller configured to control the input power to the TLCP driver to adjust the gas drive pressure,
    wherein the gas drive pressure causes the liquid in the fluid path to move at a selected flow rate when the valve pneumatically couples the pressures in the gas reservoir and the fluid reservoir, and
    the power controller is configured to control the input power to the TLCP driver to adjust the gas drive pressure to achieve the selected flow rate.

3. The system of claim 1, further comprising a volume calculation engine that calculates fluid flow as a function of a corresponding change in the input power as pressure remains substantially constant.

4. The system of claim 1, wherein the gas drive pressure is adjusted as a function of the amount of pressure in one or both the gas reservoir and the fluid reservoir.

5. The system of claim 1, wherein the TLCP driver is formed from piezoelectric material.

6. The system of claim 5, wherein the TLCP driver comprises a microblower.

7. The system of claim 1, wherein the gas-fluid interface comprises a flexible membrane that imposes no stretching forces.

8. The system of claim 1, further comprising a second valve configured to selectively isolate or pneumatically couple the TLCP driver and the gas reservoir.

9. The system of claim 2, wherein the power controller is operably coupled with the pressure sensor to receive the amount of pressure in one or both the gas reservoir and the fluid reservoir.

10. A method of determining fluid flow characteristics in a liquid delivery system comprising:
    producing a gas drive pressure at a given value from a tightly load-coupled pneumatic driver (a "TLCP" driver) by providing an input power to move gas into a gas reservoir having a known volume, the gas drive pressure configured to move fluid in a fluid reservoir;
    measuring the pressure in the gas reservoir to provide a gas reservoir pressure;
    measuring the pressure in the fluid reservoir to provide a fluid reservoir pressure;
    pneumatically coupling the gas reservoir and a fluid reservoir by opening a valve therebetween so that the gas reservoir pressure and the fluid reservoir pressure become substantially the same;
    measuring a pressure in the gas reservoir and/or the fluid reservoir after the gas reservoir and the fluid reservoir are pneumatically coupled;
    calculating a pressure change in the gas reservoir;
    calculating a pressure change in the fluid reservoir; and
    calculating the volume of liquid within the fluid reservoir as a function of the pressure change in the fluid reservoir and the gas reservoir.

11. The method as defined by claim 10, further comprising:
    pneumatically isolating the gas reservoir and the fluid reservoir by closing the valve therebetween; and
    measuring the pressure change in the fluid reservoir as fluid flows through a fluid path to determine flow rate.

12. The method as defined by claim 10, further comprising:
    detecting an occlusion in the fluid path by measuring a change in the input power that is used to maintain the gas drive pressure at the given value.

13. The method as defined by claim 10, further comprising;
    detecting a change in work output of the TLCP driver of 0.1 to 1.0 percent; and
    controlling the input power to the TLCP driver to maintain constant work output.

14. The method as defined by claim 10, wherein the TLCP driver is a microblower.

15. A computer program product for use on a computer system for precision liquid delivery, the computer program product comprising a tangible, non-transient computer usable medium having computer readable program code thereon, the computer readable program code comprising:

program code for providing an input power to a tightly load-coupled pneumatic driver (a "TLCP driver") to produce a gas drive pressure that moves gas into a gas reservoir, the gas reservoir being pneumatically coupled with a fluid path that receives a fluid drive pressure from the gas drive pressure at an interface;

program code for causing one or more pressure sensors to measure pressure in the gas reservoir and the fluid reservoir (a) prior to pneumatically coupling the gas reservoir and the fluid reservoir, and (b) after pneumatically coupling the gas reservoir and the fluid reservoir; and program code for computing a volume of unknown liquid in the fluid reservoir.

16. The computer program product of claim 15, further comprising:

program code for computing flow rate out of the fluid reservoir.

17. The computer program product of claim 16, wherein the flow rate calculation is performed by (a) measuring pressure drops in the fluid reservoir and correlating the pressure drops to flow rate, and/or (b) recalculating the volume in the fluid reservoir at a later time.

18. The computer program product of claim 15, further comprising:

program code for controlling the input power to the TLCP driver to adjust the gas drive pressure as a function of the amount of pressure in the gas reservoir and/or the fluid path to maintain the gas reservoir and/or the fluid path at a selected level.

19. The computer program product of claim 15, further comprising:

program code for detecting an occlusion in the fluid path by measuring a change in the input power that is used to maintain the gas drive pressure at the given value.

20. The computer program product of claim 15, wherein a change in fluid flow from the fluid path causes a corresponding change in the input power to the TLCP driver to maintain the gas drive pressure and the fluid drive pressure constant.

\* \* \* \* \*